United States Patent [19]

Van Geem et al.

[11] Patent Number: 5,336,810
[45] Date of Patent: Aug. 9, 1994

[54] HYDROGENATION OF BENZOIC ACID AND CATALYST SUITABLE THEREFOR

[75] Inventors: Paul C. Van Geem, Schinnen; Xiaoding Xu, Delft; Joseph J. F. Scholten, Sittard, all of Netherlands

[73] Assignee: DSM N.V., Netherlands

[21] Appl. No.: 52,358

[22] Filed: May 7, 1993

[30] Foreign Application Priority Data

May 7, 1992 [NL] Netherlands .................. 9200817

[51] Int. Cl.$^5$ ............... C07C 45/27; C07C 45/00; B01J 31/00; B01J 37/00
[52] U.S. Cl. ................... 568/435; 568/425; 568/426; 502/102; 502/104
[58] Field of Search ............. 568/426, 425, 435; 502/102, 104

[56] References Cited

U.S. PATENT DOCUMENTS 5,254,520 10/1993 Sofianos .................. 502/307

Primary Examiner—Werren B. Lone
Attorney, Agent, or Firm—Cushman, Darby & Cushman

[57] ABSTRACT

The invention relates to a catalyst that is very suitable for the conversion of a benzoic acid into the corresponding benzaldehyde. The catalyst can be obtained via coprecipitation of a manganese salt, a salt from which an acid support is formed, a zinc salt and optionally a copper salt at a pH between 4 and 10, calcination, after precipitation, of the coprecipitate at a temperature of between 300 and 700° C. and then, optionally, reduction of the calcined coprecipitate with the aid of a hydrogen-containing gas mixture. Using such a catalyst the hydrogenation of a benzoic acid can be carried out at lower temperature resulting in energy-savings and, hence, cost-savings.

14 Claims, No Drawings

HYDROGENATION OF BENZOIC ACID AND CATALYST SUITABLE THEREFOR

FIELD OF THE INVENTION

The invention relates to a catalyst suitable for hydrogenating a benzoic acid to a corresponding benzaldehyde, and a process using that catalyst.

BACKGROUND INFORMATION

A hydrogenation process conducted in the presence of a catalyst containing manganese on an acid support is described in U.S. Pat. No. 4,987,265. This catalyst is prepared via (a) coprecipitation, at a pH between 7 and 10, of a manganese salt and a salt from which an acid carrier is formed, (b) subsequent calcination at a temperature between 300° C. and 700° C., and (c) reduction with a hydrogen containing gas mixture. A hydrogenation according to U.S. Pat. No. 4,987,265 enables the production of a very high yield of benzaldehyde in the gas phase.

It has long been desired to develop means for converting benzoic acids to their corresponding benzaldehydes in the gas phase at relatively low temperatures, i.e below about 400–450° C. Significant increases in conversion and selectivity rates at such lower temperatures have also been a long sought objective. Heretofore, however, the prior processes have suffered from several drawbacks, including reduced conversion and selectivity when such hydrogenations are conducted in the gas phase below about 400° C. Indeed, at such lower temperatures, prior art processes can typically produce significant, and highly undesired, yields of such by-products as toluene, benzene, and benzyl alcohol.

SUMMARY AND OBJECTS OF THE INVENTION

The present invention comprises a catalyst obtained by coprecipitating a manganese salt, a second salt from which an acid support is formed, a zinc salt, and, optionally, a copper salt at a pH of from about 4 to 10; calcining the thus obtained co-precipitate at a temperature of from about 300° C. to about 700° C.; and then, if desired, reducing the calcined coprecipitate in the presence of a hydrogen-containing gas.

The aforementioned catalyst can be efficaciously used to promote the gas phase hydrogenation of a benzoic acid to a corresponding benzaldehyde. This process can be advantageously conducted at relatively lower temperatures, e.g. below 400° C. For instance, this hydrogenation process unexpectedly exhibits 100% conversion at temperatures below 400° C., and also exhibits higher selectivity to the desired benzaldehyde at those relatively lower temperatures, as well as at higher temperatures, such as 400° C. to 700° C.

The process yields substantial cost-savings as well as energy savings by being conductible with such high conversion and selectivity at a relatively lower temperature.

DETAILED DESCRIPTION OF THE INVENTION

The inventors have discovered that the selectivity and activity of a catalyst useful in, for example, the hydrogenation of a benzoic acid to a corresponding benzaldehyde at lower reaction temperatures can be unexpectedly enhanced through the use of at least one zinc salt promoter. The effects attributable to the presence of zinc can be enhanced by including copper in the catalyst. If zinc or zinc and copper are used as promoters, the hydrogenation reaction can be carried out at a temperature between 275° C. and 450° C., preferably between 300° C. and 400° C. The reaction is mostly carried out at atmospheric pressure or at a slightly elevated pressure, e.g. up to 10 bar.

The present invention is particularly important because the higher selectivity and 100% conversion rates permit manufacture of a benzaldehyde from a benzoic acid at lower temperatures, such as below about 400° C., while reducing, if not preventing, the undesired formation of by-products such as toluene, benzene and benzyl alcohol.

The catalyst used is an oxide of manganese, zinc and optionally copper on an acid support in the form of an oxide.

As a salt from which an acid support is formed, a salt can be used from which, for example, oxides of aluminum, zirconium, titanium, cerium, hafnium and/or niobium, preferably of aluminum, are formed in the catalyst preparation. Preferably a nitrate salt of such an element is used. A suitable coprecipitator is, for example, $NH_4OH$ or $K_2CO_3$.

The catalysts usually contain 2 to 40 wt. % manganese, calculated as metal with respect to the total amount of catalyst. The catalyst preferably contains 10 to 30 wt. % manganese. The catalysts moreover usually contain more than 10 wt. % of the metal, the oxide of which forms the acid support, e.g., Al, calculated as metal with respect to the total amount of catalyst, preferably 20 to 40 wt. %, and more than 1 wt. % Zn, calculated as metal with respect to the total amount of catalyst, preferably 15 to 50 wt. %, and particularly 20 to 45 wt. %. The amount of Cu calculated as metal with respect to the total amount of catalyst mostly is lower than 5 wt. %, preferably 0.5 to 2 wt. %.

The process for the preparation of the catalyst using zinc and optionally copper does not differ substantially from the process for making a catalyst without these promoters. Such a process as well as a hydrogenation process are described in U.S. Pat. No. 4,987,265, the complete disclosure of which is incorporated herein by reference. The present catalyst is highly suitable for the conversion of a benzoic acid into a corresponding benzaldehyde and is obtainable by coprecipitating a manganese salt, a salt, e.g. $Al(NO_3)_3$, from which an acid support e.g. $Al_2O_3$ is formed, a zinc salt and optionally a copper salt at a pH between 4 and 10, preferably 5–8; calcining at a temperature of between 300° C. and 700° C.; and then, optionally, reducing the calcined coprecipitate with the aid of a hydrogen-containing gas mixture. The reduction with the aid of a hydrogen-containing gas mixture can also be carried out in situ under the hydrogenation reaction conditions. The soluble zinc salts are mostly added to an aqueous solution of manganese salt, after which metal hydroxides are coprecipitated.

Suitable zinc compounds are, in particular, soluble zinc salts such as, for instance, zinc nitrate, zinc sulphate, zinc chloride, zinc acetate.

Suitable copper compounds are, in particular, soluble copper salts such as, for instance, copper nitrate, copper chloride, and copper sulfate.

Suitable manganese salts are, in particular, soluble manganese salts such as, for instance, manganese nitrate, manganese chloride, manganese bromide, manganese (II) sulphate, although manganese nitrate is preferred.

The present manganese oxide catalysts modified with at least the zinc promoter are suitable for the preparation of all kinds of benzaldehydes through hydrogenation of the corresponding benzoic acid. The benzoic acid may, for example, be substituted in one or more places in the aromatic ring with an alkyl group containing 1–6 carbon atoms, an alkoxy group containing 1–6 carbon atoms, a hydroxyl group and a halogen atom. Other substituents may also be present and are possible. The substituents can be at the ortho, meta and para positions of the aromatic ring. Examples of suitable benzoic acid compounds are o-Cl-benzoic acid, m-Cl-benzoic acid and p-tert-butyl-benzoic acid. As used herein, and unless stated otherwise in the application, "benzoic acid" will be understood to include substituted benzoic acid.

The hydrogenation of benzoic acid can be carried out under the influence of a hydrogenation catalyst according to the present invention in the presence of a gas mixture containing hydrogen. It can be carried out both batch wise and continuously.

After the hydrogenation of the benzoic acid, the gas mixture may be cooled in order to condense the reaction products and excess hydrogen is recirculated. The water and any benzene formed in the hydrogenation may be removed in an azeotropic drying column, after which benzaldehyde may be distilled.

The invention is explained with reference to the following, non-limiting, examples.

EXAMPLES

Preparation of the Catalyst

Catalysts were prepared by dissolving $Mn(NO_3)_2.4H_2O$, $Al(NO_3)_3.3.9H_2O$, $Cu(NO_3)_2.5H_2O$ and $Zn(NO_3)_2.6H_2O$ in water to obtain a 1M solution (relative to nitrate). Then a precipitate was formed by adding a 1M solution of $K_2CO_3$ or $NH_4OH$ to the solution under the conditions indicated in Table 1.

After filtration and drying the catalyst was reduced and screened to obtain 1–3 -mm large particles. Then the catalyst was calcined at 200° C. for 2 hours, followed by calcination at 500° C. for 3 hours.

The compositions of these catalysts are as indicated in Table 1. Table 2 shows the results of a metal element analysis in wt %.

TABLE 1

| No. | catalyst preparation solution | | | composition |
|---|---|---|---|---|
| | pH | temp. (°C.) | base | |
| 1 | 7.0 | 45 | $K_2CO_3$ | $MnO_2/0.1\ CuO$ $1.1\ ZnO.ZnAl_2O$ |
| 2 | 7.0 | 45 | $K_2CO_3$ | $MnO_2/ZnAl_2O_4$ |
| 3 | 7.0 | 45 | $K_2CO_3$ | $MnO_2/ZnO\ ZnAl_2O_4$ |
| 4 | 5.0 | 80 | $K_2CO_3$ | $MnO_2/ZnO\ ZnAl_2O_4$ |
| 5 | 8.0 | 45 | $NH_4OH$ | $MnO_2/ZnO\ ZnAl_2O_4$ |
| 6 | 7.0 | 45 | $NH_4OH$ | $MnO_2/Al_2O_3$ |

TABLE 2

| Cat. No. | Mn | Zn | Al | Cu |
|---|---|---|---|---|
| 1 | 10.6 | 27.0 | 22.5 | 1.2 |
| 2 | 11.2 | 26.6 | 23.1 | — |
| 3 | 11.2 | 36.0 | 15.8 | — |
| 4 | 3.5 | 42.5 | 19.0 | — |
| 5 | 13.0 | 31.0 | 19.8 | — |
| 6 | 10.1 | — | 36.1 | — |

EXAMPLES I–XI

The benzoic acid was introduced into a saturator that was maintained at a temperature of 150° C. Hydrogen and nitrogen were added to the saturator containing benzoic acid.

A reactor with a diameter of 8 mm was provided with 5 ml of catalyst having a particle size of between 0.5 and 0.8 mm. The reactor was heated to a temperature of between 300° C. and 450° C. with the aid of a tube furnace. The feed rate of the hydrogen was 35 Nl/h and that of the nitrogen was 4.75 Nl h. The actual contact time of the reaction mixture was 0.2 seconds at 350° C. After the reactor the product stream (to which a DMF flow of 6.9 g/h had been added after the reaction) was collected in two coolers of 15 and ~3° C. for 30 minutes. Then the components were analyzed.

Table 3 shows the temperature at which the reaction was carried out and the results that were obtained with catalysts 1–6.

TABLE 3

| Ex | Cat. | Temp. (°C.) | selectively towards benzaldehyde | degree of conversion of benzoic acid |
|---|---|---|---|---|
| I | 1 | 330 | 88.3 | 98.9 |
| II | 2 | 350 | 95.2 | 85.7 |
| III | 2 | 380 | 78.2 | 100 |
| IV | 3 | 350 | 91.0 | 48.4 |
| V | 3 | 380 | 83.8 | 100 |
| VI | 4 | 350 | 95.0 | 53.2 |
| VII | 4 | 380 | 74.3 | 100 |
| VIII | 5 | 350 | 96.4 | 70.0 |
| IX | 5 | 380 | 79.7 | 100 |
| X | 6 | 414 | 84 | 89 |
| XI | 6 | 435 | 81 | 100 |

Catalysts nos. 1 through 5 are according to the present invention and contain zinc, aluminum, and manganese, whereas catalyst no. 6 contains only manganese and aluminum. When catalysts nos. 1 through 5 are used in the present process to hydrogenate a benzoic acid to a corresponding benzaldehyde, 100% conversions at high selectivity are observable at temperatures below 400° C., whereas, when catalyst no. 6 is used in such a process, a temperature greater than 400° C. was required to achieve such a conversion.

Results comparable to those obtained with catalysts nos. 1 through 5 are obtainable using other catalysts according to the present invention based on other suitable zinc salt promoters.

What is claimed is:

1. A catalyst suitable for the conversion of a benzoic acid into the corresponding benzalehyde, said catalyst being obtained by:
   (i) coprecipitating a manganese salt, a second salt from which an acid support is formed and a zinc salt at a pH between 4 and 10 wherein the amount of manganese, calculated as metal with respect to the total amount of catalyst, is 10 to 30 wt. %; and
   (ii) calcining the precipitate of step (i) at a temperature of between 300° C. and 700° C.

2. A catalyst according to claim 1, wherein the amount of zinc, calculated as metal with respect to the total amount of catalyst is, 20 to 45 wt. %.

3. A catalyst according to claim 1, wherein said acid support is formed at pH between 4 and 10 in the presence of a zinc salt and a copper salt.

4. A catalyst according to claim 3, wherein the amount of copper, calculated as metal with respect to the total amount of catalyst, is 0.5 to 2 wt. %.

5. A catalyst according to claim 1, wherein said second sale is a salt of aluminum.

6. A catalyst according to claim 5, wherein the amount of aluminum in the catalyst, calculated as metal with respect to the total amount of catalyst, is 20 to 40 wt. %.

7. A catalyst according to claim 1, wherein the manganese, second and zinc salts are nitrates.

8. A catalyst suitable for the conversion of a benzoic acid into the corresponding benzaldehyde, said catalyst being obtained by:
  (i) coprecipitating a manganese salt, an aluminum salt from which an acid support is formed, and a zinc salt at a pH between 4 and 10; and
  (ii) calcining the precipitate of step (i) at a temperature of between 300° C. and 700° C.
  (iii) in which the amounts of manganese, aluminum, and zinc, respectively, are 10 to 30 wt. %, 20 to 40 wt. %, and 20 to 45 wt. %, calculated as metal with respect to the total amount of catalyst.

9. A catalyst according to claim 8, wherein the manganese, second and zinc salts are nitrates.

10. A catalyst according to claim 8, wherein the coprecipitating step (i) is conducted in the further presence of a copper salt, and the amount of copper in the catalyst is 0.5 to 2.0 wt. %, calculated as metal with respect to the total amount of catalyst.

11. A catalyst according to claim 10, wherein the manganese, second and zinc salts are nitrates.

12. A process for hydrogenating benzoic acid or derivatives thereof comprising hydrogenating unsubstituted benzoic acid or a benzoic acid that is substituted in at least one position on the aromatic ring with an alkyl group containing 1–6 carbon atoms, an alkoxy group containing 1–6 carbon atoms, a hydroxyl group or hydrogen, in the gas phase, in the presence of a catalyst according to claim 1.

13. A catalyst according to claim 1, wherein the product of step (ii) is reduced with a hydrogen-containing gas mixture.

14. A catalyst according to claim 7, wherein the product of step (ii) is reduced with a hydrogen-containing gas mixture.

* * * * *